United States Patent [19]

Gorsuch et al.

[11] Patent Number: 4,950,224

[45] Date of Patent: Aug. 21, 1990

[54] APPARATUS AND METHOD FOR IN VIVO PLASMA SEPARATION

[75] Inventors: Reynolds G. F. Gorsuch, Yountville; John Atkin, Corona Del Mar, both of Calif.

[73] Assignee: Healthdyne, Inc., Mariette, Ga.

[21] Appl. No.: 229,007

[22] Filed: Aug. 5, 1988

[51] Int. Cl.$^5$ ........................................... H61M 37/00
[52] U.S. Cl. ........................................... 604/4; 604/6; 604/53
[58] Field of Search ..................... 604/4, 5, 6, 7, 8, 52, 604/53, 405, 406, 27, 20; 210/645, 646; 120/200.25

[56] References Cited

U.S. PATENT DOCUMENTS

| Re. 31,688 | 9/1984 | Popovich et al. | |
|---|---|---|---|
| 4,240,907 | 12/1980 | Bentley | 210/646 |
| 4,389,363 | 6/1983 | Molthop | |
| 4,498,990 | 2/1985 | Shaldon et al. | |
| 4,559,034 | 12/1975 | Kirita et al. | 604/52 |
| 4,563,170 | 1/1986 | Aigner | 604/43 |
| 4,583,969 | 4/1988 | Mortensen | 604/4 |
| 4,604,208 | 8/1956 | Chu et al. | |
| 4,623,327 | 11/1986 | Mahurkar | |
| 4,631,053 | 12/1986 | Taheri | 604/4 |
| 4,767,400 | 8/1988 | Miller et al. | 604/8 |
| 4,769,037 | 9/1988 | Midcalf | 604/5 |
| 4,790,331 | 12/1988 | Okada et al. | 604/53 |
| 4,820,261 | 4/1989 | Schmoll et al. | 604/4 |
| 4,850,950 | 7/1984 | Berry et al. | 604/26 |

FOREIGN PATENT DOCUMENTS

| 2606642 | 5/1988 | France | 604/405 |
|---|---|---|---|
| 2616666 | 12/1988 | France | 604/53 |

Primary Examiner—C. Fred Rosenbaum
Assistant Examiner—Kathleen A. Doley
Attorney, Agent, or Firm—Jones, Askew & Lunsford

[57] ABSTRACT

An apparatus for the continuous in vivo separation of plasma from other blood components comprising a bundle of microporous hollow fibers inserted into the vena cava. The fibers are sized to permit diffusion of plasma through the fiber pores but not cellular or other larger blood components. The fibers are in fluid communication with a dual lumen catheter which removes plasma from the hollow fibers to a treatment system and returns treated plasma to the bloodstream. The apparatus can be incorporated into an ambulatory plasma separator system for providing continuous plasma treatment while the user is mobile.

26 Claims, 4 Drawing Sheets

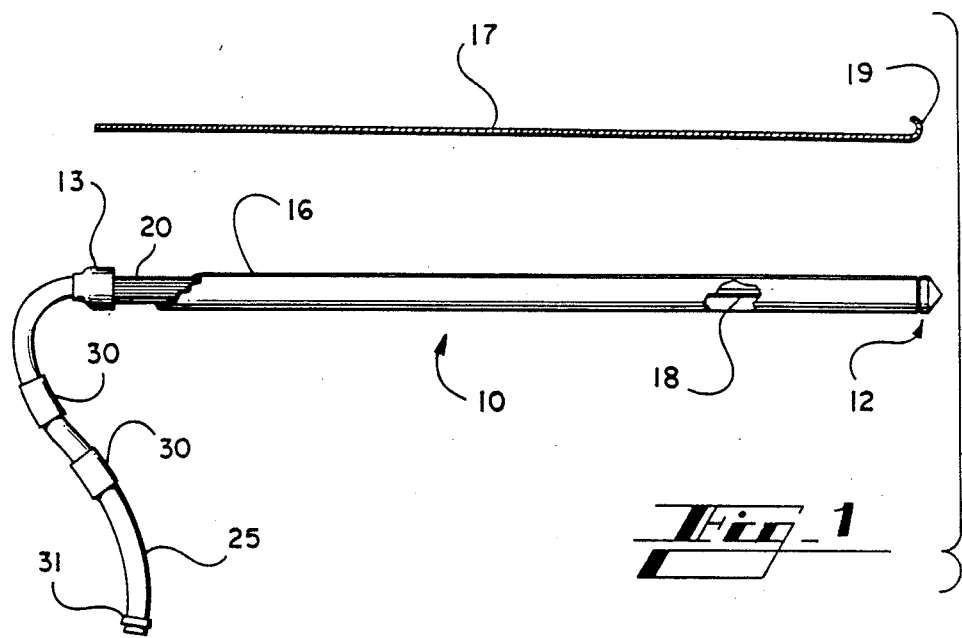
Fig_1
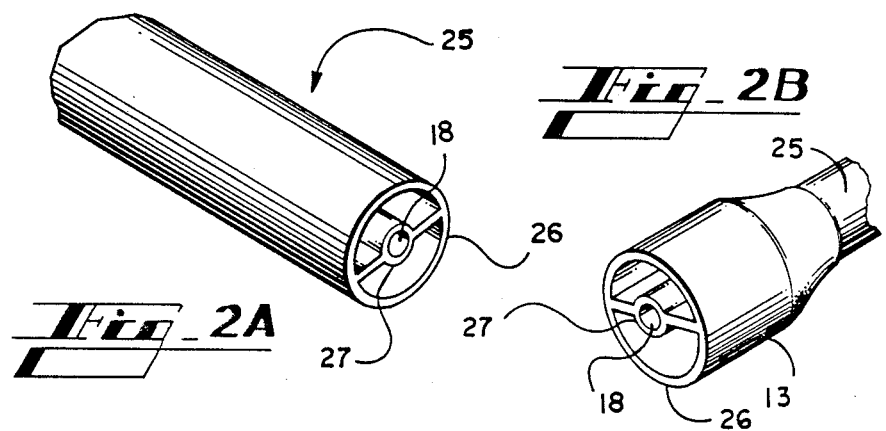
Fig_2A
Fig_2B

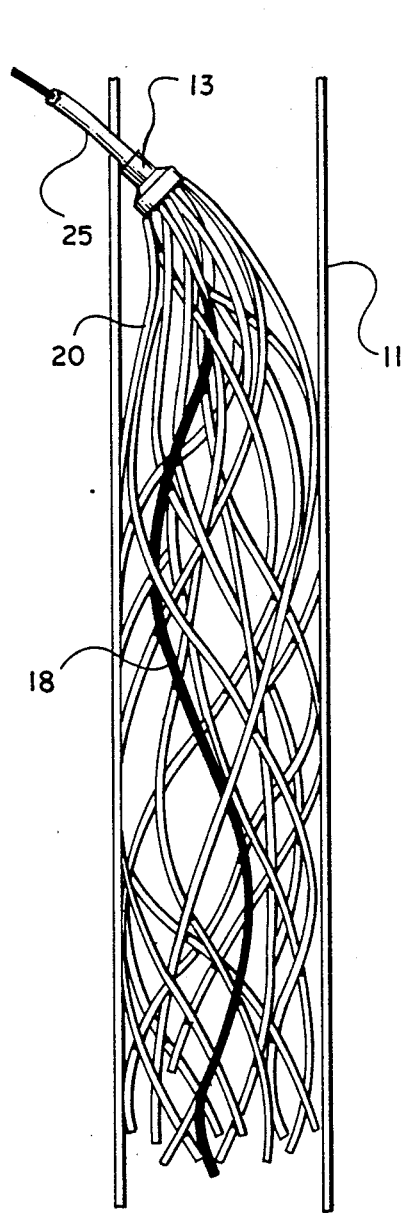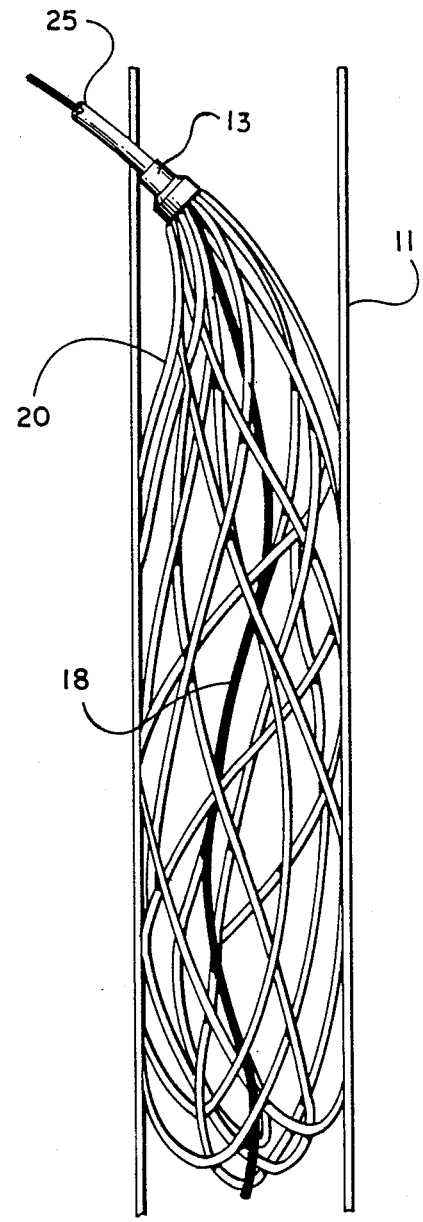
Fig_3
Fig_4

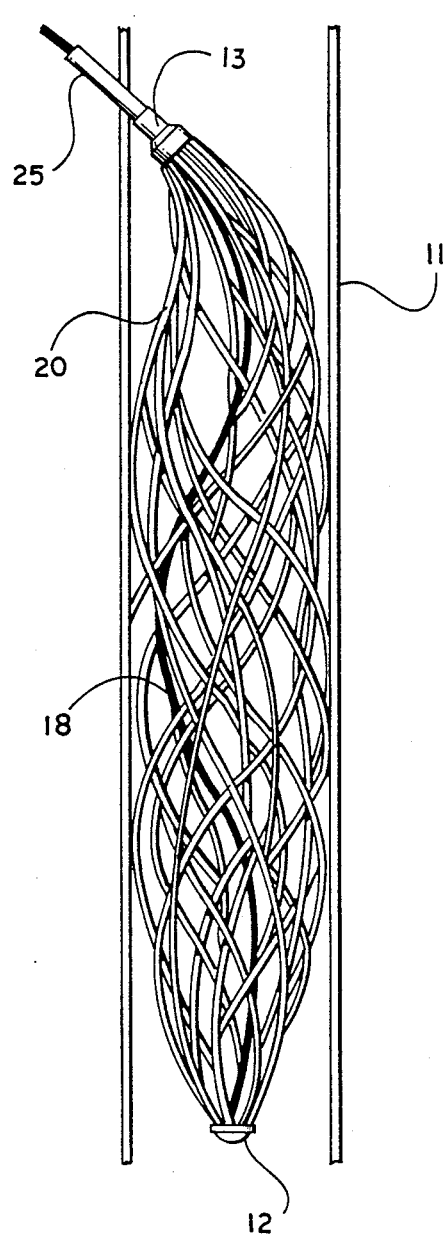
Fig_5
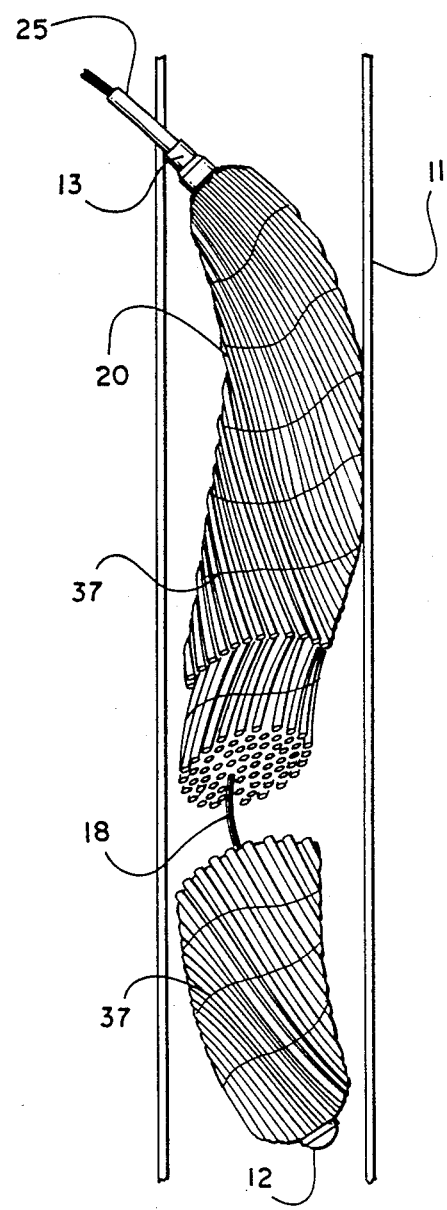
Fig_6

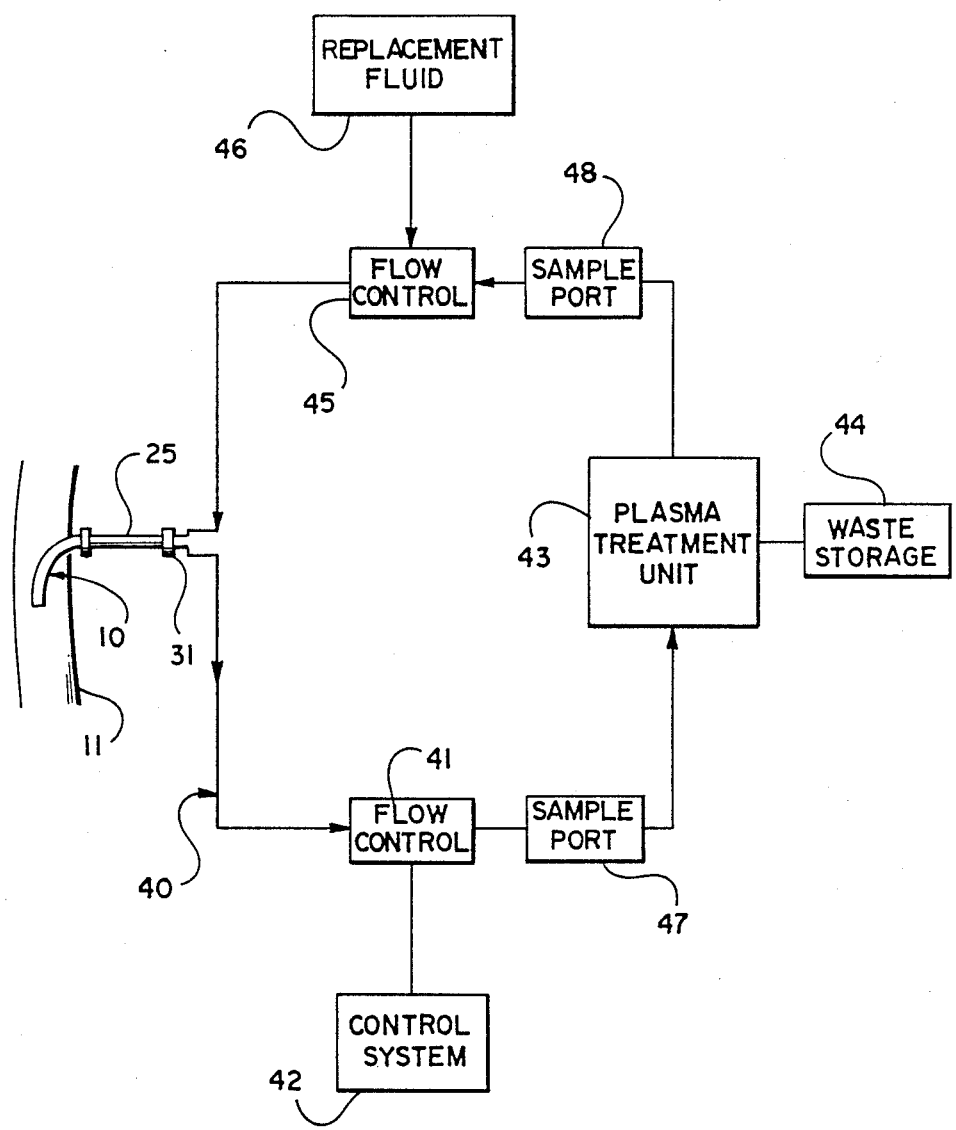

APPARATUS AND METHOD FOR IN VIVO PLASMA SEPARATION

TECHNICAL FIELD

The present invention relates to plasmapheresis, a technique for the separation of plasma from other blood components and its treatment. More particularly, the present invention is an apparatus and method for the continuous in vivo separation of plasma as well as a plasma separation and treatment system containing the apparatus.

BACKGROUND OF THE INVENTION

The term "plasma" refers to the soluble fluid portion of blood including organic substances, such as proteins, fats, sugars and other organic compounds, and inorganic substances, such as minerals. The term "plasma" does not include particulate components suchh as blood cells.

Blood is composed of a number of different components. Approximately 45% of the volume is composed of cellular matter, including red cells (erythrocytes), while cells (leukocytes) and platelets, all of which are much larger in size than plasma components. Plasma is the fluid that suspends the cellular materials and makes up the remaining 55%. It consists of approximately 90% water, 7% protein, which includes antibodies, antigens, immune complexes, pathogens, toxins, and other molecules, and 3% of various other organic and inorganic matter.

The term "plasmapheresis" is commonly defined as the removal of whole blood from the body, separation of its cellular elements by centrifugation, and reinfusion of cellular elements suspended in saline or some other plasma substitute, thus depleting the body's own plasma protein without depleting its cells (Stedman's Medical Dictionary, 24th Ed., 1982). Where treatment of the plasma and its return to the body, rather than its permanent removal, is desired, blood is withdrawn from the patient, the plasma is separated, treated, admixed with an appropriate volume of replacement fluid, and subsequently returned to the body. This technique is useful for treatment of various disease states, as discussed more fully below.

Plasma collection from donors is desirable for use in medical settings where a victim has lost large amounts of body fluids which need to be replenished. A bank or stored collection of plasma is a valuable asset to hospitals, especially those which have trauma centers or major surgery facilities. Treatment of the donor plasma to remove pathogens such as immune deficiency virus ("HIV") which causes Acquired Immune Deficiency Syndrome ("AIDS") is growing ever more important with the epidemic rise of AIDS and the increasing concern for the world's blood and plasma supply. Plasmapheresis can also be used as a diagnostic tool to detect disease-causing substances in the blood by analyzing the plasma fraction. This is especially valuable where a particular test or assay encounters interfering reactions from cellular components.

Removal of pathogenic material from a patient's blood is believed to benefit patients; e.g., removal of immune complexes is believed to be useful in the treatment of certain cancers. Numerous other conditions may possibly be treated using plasmapheresis including, but not limited to, myasthenia gravis, glomerulonephritis, Goodpasture's syndrome, pemiphigus, herpes gestationis, severe asthma; certain immune complex diseases such as crescentic nephritis, systemic lupus erythematosus, diabetic hypertriglyceridemia, hypercholesterolemia, macroglobulinemia, Waldenstrom's syndrome, hyperviscosity syndromes, paraproteinemias, myeloma, Raynaud's disease and phenomenon, thrombocytopenia, renal transplantation, rhesus incompatibility; poisons such as paraquat; Factor VIII inhibitor or antibodies, hepatic coma, preparation of immunoglobulins, human tetanus immunoglobulin, and the like.

A typical plasmapheresis system comprises a means for removing whole blood from a vein. The vein is used rather than an artery because of the high arterial pressure and surge within the vessel. Venous pressure is more constant, thereby providiing a more convenient source of blood. The whole blood is then delivered outside the body, or "extracorporeally," to a means for separating plasma from cellular components. The separated plasma is then delivered to a means for filtering, dialyzing or otherwise treating the plasma to remove undersirable components. In some cases desirable substances may be added to the plasma. If necessary, a volume of replacement fluid can be added to the plasma. The treated plasma is then reinfused into the patient. In the typical system, the plasmapheretic separation of plasma and cellular components occurs extracorporeally, after whole blood has been removed from the body. The separation is commonly done by centrifugation.

Unfortunately, typical plasmapheresis techniques can cause damage to the blood cells by subjecting them to severe shearing stresses or high pressurization which causes an interaction between the cells and the device surfaces where damage occurs to the cell membrane, and pieces of the cell are removed causing hemolysis. Moreover extracorporeal separation of blood cells increases the possibility of infection or contamination from the mechanical apparatus, technician error, environmental conditions or other sources. As centrifugation requires additional machinery to perform the separation, expensive bulky apparatus is necessary, adding to the system (and patient's) cost. Similarly, extracorporeal membrane filtration of blood increases the chance of contamination with infectious agents.

U.S. Pat. No. Re. 31,688 issued to Popovitch et al., discloses a method and apparatus for continuous plasmapheresis whereby whole blood is withdrawn from the body and separated by continuously ultrafiltering the patient's blood at specified shear stresses and membranes employing a membrane ultrafilter. The apparatus delivers whole blood for extracorporeal separation as compared to in vivo separation. The problems of contamination and damage to the red and white blood cells are present. The ultrafiltration chamber used in that invention adds additional mechanism and the use of bulky machinery prevents and ambulatory concept from being employed.

A problem in the prior art is that the plasmapheresis apparatus is larggge and difficult to trasport. Because of this limitation, a patient with a chronic problem, such as a non-functioning kidney, must be treated periodically by travelling to an appropriate yet sometimes distant facility. Typically, the kidney patient will be treated when the toxic substances in the blood reach high levels. Thus, the typical kidney patient will cycle between low levels of toxic substances immediately after dialysis to high levels of toxic substances immediately before dialysis. This cycling of toxic substances is harmful to other organs in the body.

A plasma separation method and apparatus is needed that is small and easily transportable. In addition, the plasma separation method and apparatus should be continuous in operation so that the concentration of toxic substances will not build up, but can be continuously removed. Further, such plasma separation method and apparatus should reduce the manipulations that must be performed extracorporeally thereby reducing the opportunity for infection.

SUMMARY OF THE INVENTION

In accordance with the present invention, an apparatus is provided for the continuous in vivo separation of plasma from other blood components. The apparatus comprises at least one and preferably a plurality of microporous hollow fibers implantable in a blood vessel, such as the vena cava, and having a pore size sufficient to admit plasma while preventing other blood components from entering the membrane. The membrane can be composed of polypropylene or other appropriate material.

The present invention also provides a method for on-line plasma separation with continuous removal and reinfusion of plasma, whereby plasma is continuously separated by an in vivo apparatus, and then treated by an extracorporeal treatment system. The treated plasma is then returned to the body.

Additionally, a plasma separation and treatment system is described using the apparatus to continuously separate plasma from other blood components in vivo. Such a system employs the apparatus to remove plasma from the body; the plasma is then passed through a filter or other plasma treatment means to remove or treat particular matter from the plasma. The treated plasma is then combined with a volume of replacement fluid and reinfused into the body. The system can be used in a number of situations with different modifications to the treatment means depending on the circumstances and the condition of the patient. For example, such a system can be useful in treating hypercholesterolemia by removing low density lipoproteins. Alternatively, breast cancer patients can have *Staphylococcus aureus* removed from their blood by passing the plasma through an enzyme column. This process would allow the patient's immune system to more effectively attack the cancer. Similarly, other toxins or pathogens can be removed by using the plasmapheresis system described herein, such as but not limited to viruses, bacteria, immune complexes, organic chemicals and the like.

OBJECTS OF THE INVENTION

It is therefore the object of the present invention to provide an implantable apparatus for on line in vivo plasma separation.

It is another object of the present invention to provide a hollow tubular microporous fiber membrane capable of admitting plasma through its walls while preventing other blood components from entering.

It is still another object of the present invention to provide an apparatus for use in an on line plasma separation system with continuous removal and reinfusion of plasma.

It is yet another object of the present invention to provide a method for on line plasma separation with continuous removal and reinfusion of plasma.

It is a further object of the present invention to provide a novel means for separating plasma from blood.

It is yet another object of the present invention to provide a novel means for continuously dialyzing a patient with impaired kidney function.

It is another object of the present invention to provide a plasma separation apparatus that is portable and can be carried by a patient.

It is another object of the present invention to provide a plasma separation apparatus that will reduce the incidence of infection.

These and other objects, features and advantages of the present invention will become apparent after a review of the following detailed description of the disclosed embodiment and the appended claims.

SUMMARY DESCRIPTION OF THE DRAWINGS

FIG. 1 provides a side view of an in vivo plasma separation apparatus in a preferred embodiment of the present invention.

FIGS. 2A–B provide perspective cutaway views of a preferred embodiment of a dual lumen catheter and header of the present invention.

FIG. 3 provides a section view of the apparatus when implanted in a blood vessel.

FIG. 4 provides a section view of an alternative embodiment of the present invention in which the implanted fibers are looped back to the catheter header.

FIG. 5 provides a section view of an alternative embodiment of the present invention in which the implanted fibers have a distal header.

FIG. 6 provides a section view of an alternative embodiment of the present invention in which the implanted fibers have a braided spiral configuration with cross fibers.

FIG. 7 provides a flow diagram of a plasmapheresis treatment system in a preferred embodiment of the present invention.

DETAILED DESCRIPTION OF THE INVENTION

Referring to the drawings in which like numbers represent like parts, FIG. 1 shows an in vivo plasma separator apparatus 10 comprising at least one and preferably a plurality of hollow microporous fibers 20 each having a hollow interior disposed longitudinally therein. The fibers 20 can be made of any suitable material such as polymeric plastic, but are preferably polymeric polypropylene. The fibers 20 can be made by methods known to those skilled in the art. For example, polypropylene can be mixed with a solvent and the mixture spun. As the solvent and polymer phase are separated the fiber is formed. One suitable fiber commercially available is Plasmaphan ® membranes made from polypropylene polymer (ENKA AG, Wuppertal, West Germany). The fibers 20 possess a microporous structure havng a very high void volume, low variation in pore distribution, and high reproducibility in production. The fiber pore size is sufficient to admit plasma to pass through the wall of the hollow fiber and into hollow center 22 (not shown), yet not significantly obstructing fluid flow through the blood vessel. Cellular components, however, are unable to diffuse through the fiber pores. Predominantly large molecules will pass around apparatus 10 and along within the vein fluid flow. The fluid flow also pervents the clogging of the pores. The fiber pore size can be from about 0.1 to 1.0

μm; preferably, from about 0.2 to 0.8 μm; and more preferably, from about 0.4 to 0.6 μm.

The fibers 20 are longitudinally aligned in a generally parallel or radial orientation. The plurality of fibers 20 provide a large available surface area through which plasma can diffuse. The individual fibers can be arranged in a bundle to ensure adequate fluid-membrane contact along substantially the entire exterior surface of the membrane. The fibers 20 are preferably loosely bundled so as to improve surface area contact with blood.

The inserted portion comprises a distal header 12 and a proximal header 13. When introduced within the vein 11, the apparatus 10 is situated with the proximal header 13 upstream from the distal header 12 with respect to blood flow. The fibers 20 are connected to the distal header 12 and the proximal header 13 by standard potting and cutoff techniques used in the medical industry in the manufacture of hollow fiber oxygenators and hollow fiber kidney dialysis membrane filters. In this process, the fibers are potted into a solid block of plastic or epoxy fixing their position and the block is cut transverse to the fibers exposing their open ends to a chamber for gas or fluid access. The connected fibers 20 describe a generally circular pattern at the headers 12 and 13. Within the headers is a central lumen 18, which comprises a hollow tube disposed concentrically in a generally parallel orientation with the fibers 20. The central lumen 18 carries treated plasma and replacement fluid from the extracorporeal plasmapheresis system back into the body where it exits the lumen 18 at a hole (not shown) in the distal header 12 downstream.

The fibers 20 can be oriented by design in several different configurations, as illustrated by FIGS. 3-6. FIG. 3 shows a free flow single-ended apparatus 10 inserted within the vein 11. The distal header 12 need not be present, thereby allowing the closed distal ends of the fibers 20 and the open ended central lumen 18 to be suspended in the blood fluid. In this instance the central lumen 18 can be semipermeable along its length to permit diffusion of fluids back into the bloodstream. The distal ends of the fibers 20 are closed so that plasma can enter the fiber interior channel by diffusion through the fiber pores, yet not be drawn out the distal ends downstream.

FIG. 4 shows a continuous loop design whereby both ends of each of the fibers is connected to the proximal header 13. In this embodiment there would be no need for a distal header 12. The central lumen 18 floats freely with its distal end open so as to return treated plasma downstream.

FIG. 5 illustrated an expanded dual header apparatus 10 having the distal header 12 in place and connected to the central lumen 18 which can be perforated along its length. The fibers 20 are loosely intertwined. The central lumen 18 is open at its distal end and the connection to the distal header 12 permits fluid flow from the central lumen 18 downstream in the vein 11 from the fibers 20.

FIG. 6 depicts a performed braided configuration where the fibers 20 are arranged in a spiral twist configuration. The fibers 20 are held together loosely by at least one and preferably a plurality of cross fibers 37. The cross fibers 37 are preferably solid multifilament fibers disposed transverse to the fibers 20.

In all the above embodiments the fibers 20 and the central lumen 18 are placed prior to insertion within an insertion sheath 16, which comprises a hollow tube open at both ends. The sheath 16 permits easier introduction within the vien 11 by containing the apparatus 10 in a semi-rigid position.

A guide wire 17 disposed within the central lumen 18 enhances insertion of the apparatus 10 into the vein 11 without additional perforation of the wall of the vein 11. The wire 17 is a generally straight length of flexible yet stiff material such as plastic or metal. A hook 19 at one end of wire 17 is flexible so as to facilitate passage within the vein 11, yet when pulled out the hook will flex to a more straightened orientation so as to avoid puncturing or embedding in the vein wall.

A multi-lumen catheter 25 is connected to the proximal header 13 and in a preferred embodiment is composed of a hollow outer tube 26 in which resides coaxially a smaller concentric hollow inner tube 27, as shown in FIG. 2A. The inner tube 27 is in fluid communication with the central lumen 18. The outer compartments of the tube 26 are in fluid communication with the fibers 20. Plasma from apparatus 10 passes from the body through the walls of fibers 20 and along the channel defined by the inner wall of the outer compartments of the tube 26 of the outer wall of the inner tube 27. FIG. 2B illustrates the header 13 utilizing the two coaxial lumens 26 and 27 which connects the fibers 20 and the central lumen 18 to the catheter 25. Treated plasma from the system reenters the body through the inner tube 26. The catheter 25 is composed of any suitable non-reactive flexible impermeable material such as plastic, with silicone or polyurethane being preferred. It is to be understood that the fluid flow can be arranged so that plasma from the body could alternatively pass through the inner tube 26 and return through outer tube 27.

It is understood that various other head configurations are available and will suffice with the present invention.

Located within the catheter 25 is at least one and preferably a plurality of anti-bacterial barriers 30 composed of a nonreactive porous meterial having a relatively uniform pore size sufficient to prevent bacteria from passing through the barriers yet permitting smaller molecules to pass therethrough. The barriers 30 minimize contamination of in vitro equipment.

The apparatus 10 is placed in the superior vena cava via the subclavian vein or the cephalic vein using standard Brovial technique known in the art and not detailed here. Briefly, however, an incision is made in the skin and a second incision is made in the superior vena cava. The guide wire 17, which is placed within the distal header 12 opening of the central lumen 18, is inserted in the vein 11 first as an insertion aid to lead the sheathed apparatus 10 into the vein 11. After the apparatus is in place, the guide wire 17 is removed from the proximal header 13 end and the insertion sheath 16 is similarly removed. The fibers 20 separate from each other somewhat within vein 11 and increase the fiber surface area in contact with the blood. Alternatively, the apparatus 10 may be introduced via the femoral or jugular vein.

Plasma separation is accomplished within the vein 11 by blood coming in contact with the fiber 20. Plasma fluid and dissolved molecules can diffuse through the membrane and into the hollow center. Diffusion can occur passively or by means of external negative pressure such as pumping means connected to the catheter 25.

A general system for plasma treatment is shown in FIG. 7 wherein the plasma separator apparatus 10 located in the superior vena cava 11 continuously separates plasma from cellular components. After removal from the body, plasma travels through a connector 31 which places the catheter 25 in fluid communication with a tube 40 and through a flow control 41, which can be a regulated pumping means to motivate the flow of fluid within the in vitro system. A mocroprocessor-controlled system 42 regulates and monitors fluid flow. Plasma is passed into a plasma treatment unit 43, which can contain any of a number of different treatment or detoxification systems, as described more fully herein below.

The underlying principal for the separation of subcomponents from plasma fluid is based on the difference in molecular size, charge, polarlity, pH, structure or some other characteristic of the subcomponent to be separated. The treatment unit 43 can be any one of several filtration or treatment mechansims, such as but not limited to filtration, exchange columns, dialysis, enzyme columns, a series of columns, or the like.

Where the pathogenic materials such as viruses or immune complexes are to be removed, filter membranes of defined pore size can be used to retain only molecules of a size corresponding to the pathogen of interest while permitting smaller molecules to pass through. The various separation procedures that can be used in conjunction with the plasmapheresis apparatus of the present invention are well known to those of ordinary skill in the art. Material removed from the plasma can be stored in a waste storage container 44.

Alternatively, an antibody directed against the pathogen can be immobilized on a solid surface and the plasma contacted therewith. When the pathogen comes in contact or proximity with the immobilized antibody a complex is formed, thereby removing the pathogen from the plasma fluid.

Examples of conventional plasma treatment methods useful in connection with the present invention include, but are not limited to, ion exchage, fractionation, single or multiple filtration, cryoprecipitation, salt precipitation, adsorption or dialysis. Any of these techniques can be designed for use with the plasma treatment 43 of the present invention.

After separation or treatment, the processed plasma is passed to an optional flow control 45 where an optional replacement fluid 46 can be admixed with the plasma. The fluid 46 can be any neutral biocompatible fluid such as saline or the like. This plasma is then continuously returned to the body through the inner tube 26 which is in fluid communication with the central lumen 18. The continuous nature of the process ensures a relatively constant body fluid level and alleviates trauma to the body which can occur with batch processes.

Sample ports 47 and 48 are provided for removing aliquots of fluid for analysis.

In a particular embodiment of the present invention designed to treat hypercholesterolemia (high cholesterol), plasma is removed from the body via the plasma separator apparatus 10 and passes over a heparinagarose or low density lipoprotein-antibody-linked sepharose column in treatment unit 43 resulting in selective binding of low density lipoproteins.

In an alternative embodiment, the treatment unit 43 can be designed to treat neoplastic diseases by immunoadsorption. Circulating immunoglobulins or immune complexes have been implicated in the pathogenesis of cancer. These molecules are thought to act as "blocking factors" in animals and patients with tumors, suppressing the ability of the host's immune system to destroy tumor cells. It has been shown in a number of systems that sera from cancer patients and from tumor-bearing animals suppress a number of immunological functions in vitro and would therefore provide an atmosphere which should facilitate the growth of tumor cells. It is postulated that immunological mediation in cancer has a major role in a tumor's escape from host immunological control and that procedures to remove them might be therapeutically useful. *Staphlococcus aureus* Cowans I bears on its surface protein A that has the capacity to react with the Fc region of IgG from human and many mammalian species, and to combine with immune complexes in serum.

Continuous flow extracorporeal filtration of plasma over heat-killed, formalin-treated *S. aureus* in a column within treatment unit 43 was utilized to treat a patient with metastatic colon carcinoma and dogs with spontaneous cancers. This treatment was shown to cause significant tumor regression. A reduction is serum blocking activity and reduced immune complexes appear to allow a subsequent tumor specific immune response. This approach has been extended to five women with breast adenocarcinoma and in three of the five cases an objective partial remission was observed. Similar therapeutic success has been reported with plasma profusion over Protein A in patients with breast cancer.

Another preferred embodiment of the present invention is used in a cascade filtration system whereby plasma that has been removed from the vein via apparatus 10 is passed through one or more membranes of various porosities for use in the selective removal of macromolecules from the plasma. This embodiment allows for the selective removal of immune complexes, albumin or lower molecular weight plasma fractions, including low density lipoproteins.

In yet another embodiment of the present invention a wearable artificial kidney pack is designed incorporating the plasma separator apparatus 10 for use in various treatments such as hemodialysis with End Stage Renal Disease patients or the like. The pack comprises a small, hollow fiber dialyzer together with plasma and dialystic pumps. After separation and removal from the body by apparatus 10 plasma is passed through a suitable cartridge such as Sorbtion and a concentrate infusate. The cartridge consists of five layers: an enzyme, such as urease; an adsorbent, such as activated carbon; a cation exchanger, such as zirconium phosphate; and an anion exchanger, such as hydrated zirconium oxide. When spent dialysate is passed through this cartridge urea is converted by the urease to ammonium carbonate. The ammonium ion is adsorbed by the zirconium phosphate in exchange for sodium and hydrogen ions. The hydrogen ions combine with carbonate to form bicarbonate, carbon dioxide and water. Potassium, calcium and magnesium are also adsorbed by the zirconium phosphate is exchange for sodium. Phosphate is adsorbed by the hydrated zirconium oxide in exchange for acetate. Creatinine, uric acid and other organic compounds are adsorbed by the activated carbon. As a result of these processes, the effluent from the cartridge contains sodium chloride, sodium bicarbonate and sodium acetate. An infusate system consisting of a concentrate and pump adds potassium, calcium and magnesium, as the acetate salts, to the effluent, resulting in a regenerated dialysate.

Separated plasma is removed from the body through one lumen and treated plasma is re-infused into the patient's bloodstream through the other lumen.

These are numerous advantages to in vivo plasma separation with extracorporeal treatment. This on-line plasma separation and treatment is carried out continuously. The patient does not have the peaks and corresponding troughs that are associated with conventional plasmapheresis techniques such as dialysis, where the patient must physically travel to a facility each week or, at a recommended time, be hooked up to a machine and then be processed. Continuous treatment at any physical locale at any time is more beneficial to the patient's well being. A resident catheter 25 is also more likely to cause less upset and pain to the user than regular venipunctures. The present invention possesses fewer biocompatibility problems, since the blood is not exposed to external surfaces, and the catheter construction is from highly biocompatible materials, such as silicone or polyurethane. Continuous processing provides improved efficacy of drug therapy or treatment in an ambulatory system using a portable plasma separation device versus batch processing using expensive and bulky equipment. Less upset to the patient occurs with continuous pocessing than with batch because body fluid levels are kept more near to normal. In vivo plasma separation reduces damage to red blood cells and possible infection or contamination. Passive plasma diffusion through the membrane ensures gentle separation of fragile blood components.

Continuous process permits downsizing of system components because the flow rate through the system is lower, thus reducing the capacity requirement for any component in terms of function per unit time. The use of microchip processors permits accurate control over apparatus functions without consuming much space.

Extracorporeal separation permits the use of agents which, if used in vivo, would be toxic or otherwise harmful. This invention allows for treatment modalities impractical by other means.

It should be understood that the foregoing relates only to preferred embodiments of the present invention and that numerous modifications or alterations may be made therein without departing from the spirit and the scope of the invention as set forth in the appended claims.

We claim:

1. An apparatus for continuous in vivo plasma separation, comprising:
   at least one elongated microporous fiber having a hollow interior, said fiber being dimensioned to be received within a blood vessel without significantly obstructing fluid flow through said blood vessel, the pore size of said fiber being sufficient to allow plasma to diffuse through said pores into said hollow interior of said fiber but not sufficient to allow cellular components larger than plasma to diffuse therethrough; and
   said hollow interior of said elongated fiber being in fluid communication with a means for conducting plasma comprising a first discrete hollow tube which connects to one end of the fiber and permits passage of plasma from said hollow interior of said fiber and a second discrete hollow tube which returns plasma to said blood vessel such that plasma being removed from said fiber is kept separated from plasma being returned to the blood vessel.

2. The apparatus of claim 1 wherein said fiber is composed of a polymeric material.

3. The apparatus of claim 2 wherein said polymeric material is polypropylene.

4. The apparatus of claim 3 wherein said fiber has a pore size of from about 0.1 to 1.0 $\mu$m.

5. The apparatus of claim 3 wherein said fiber has a pore size of from about 0.2 to 0.8 $\mu$m.

6. The apparatus of claim 3 wherein said fiber has a pore size of from about 0.4 to 0.6 $\mu$m.

7. The apparatus of claim 1, wherein said at least one elongated microporous hollow fiber comprises a plurality of elongated microporous hollow fibers, said plurality of fibers being dimensioned to be received within a blood vessel without significantly obstructing fluid flow through said blood vessel.

8. The apparatus of claim 2, wherein said second tube includes means returning the plasma to said blood vessel downstream from said fibers within the blood vessel, such that said returned plasma does not immmediately diffuse back into said fibers.

9. The apparatus of claim 8, wherein said pair of tubes comprise a dual lumen catheter.

10. The apparatus of claim 9, wherein said tubes are disposed substantially parallel to one another.

11. The apparatus of claim 9, wherein said tubes are disposed co-axially relative to one another, such that the inner passage defines a central lumen and the outer passage defines an outer lumen.

12. The apparatus of claim 11, wherein said central lumen returns plasma from said plasma receiving means to said blood vessel through an opening in said central lumen which extends downstream in said fluid flow from said fibers, whereby said returned plasma is not immediately diffused back into said fibers.

13. The apparatus of claim 7, further comprising a connector means for placing said fibers in fluid communication with said pair of tubes comprising a header.

14. The apparatus of claim 1, further comprising a removable sheath which surrounds said fibers to facilitate insertions of said fiber into said blood vessel, said sheath being removable from said fiber within the blood vessel to expose said fiber to fluid.

15. The apparatus of claim 14, further comprising a flexible elongated guide wire removably disposed within said sheath for facilitating insertion of said fiber into said blood vessel.

16. The apparatus of claim 1, further comprising a treatment system in fluid communication with said fiber, whereby selected subcomponents of said plasma removed from said blood vessel are treated and the treated plasma returned to said blood vessel.

17. The apparatus of claim 16, further comprising means for admixing said treated plasma with an amount of fluid prior to returning said plasma to the blood vessel.

18. The apparatus of claim 17, wherein the amount of said fluid admixed with said treated plasma is sufficient to approximate the volume of plasma removed from said blood vessel prior to treatment by said plasma receiving means, whereby the volume of fluid in the body is kept approximately constant.

19. The apparatus of claim 18, wherein said fluid comprises saline.

20. The apparatus of claim 1, further comprising a pumping means for motivatng diffusion of said plasma through said fiber into said hollow interior of said fibers.

21. The apparatus of claim 20, wherein said pumping means comprises means for generating a negative pressure within said hollow interiors of said fiber.

22. The apparatus of claim 21, wherein said negative pressure generating means comprises a vacuum pump, such that said pump creates a pressure drop across said microporous fiber facilitating the passage of plasma through said fiber into said hollow interior of said fibers.

23. A method for continuous in vivo plasma separation, comprising the steps of:
(a) implanting in a blood vessel at least one elongated microporous fiber having a hollow interior, said elongated fiber being dimensioned to be received within a blood vessel without significantly obstructing fluid flow through said blood vessel, the pore size of said elongated microporous fiber being sufficient to allow plasma to diffuse through said pores into said hollow interior of said fiber but not sufficient to allow cellular components larger than plasma to diffuse therethrough;
(b) placing said hollow interior of said elongated fiber in fluid communications with a means for conducting plasma comprising a first discrete hollow tube which connects to one end of the fiber and permits passage of plasma from said hollow interior of said fiber, and a second discrete tube which returns plasma to said blood vessel such that plasma being removed from said fiber is kept separated from plasma being returned to the blood vessel;
(c) removing plasma from said blood vessel;
(d) treating said plasma to remove or treat selected subcomponents of said plasma; and
(e) re-infusing said plasma into said blood vessel.

24. The method of claim 23, further comprising the step of admixing a volume of replacement fluid with said treated plasma to re-infusion into said blood vessel.

25. The method of claim 23, wherein said blood vessel is the vena cava.

26. The method of claim 25, wherein said blood vessel is the superior vena cava.

* * * * *